United States Patent [19]

Streuff et al.

[11] Patent Number: 4,601,895

[45] Date of Patent: Jul. 22, 1986

[54] DELAYED-ACTION ACETYLSALICYLIC ACID FORMULATIONS FOR ORAL ADMINISTRATION

[75] Inventors: Bernhard Streuff, Cologne, Fed. Rep. of Germany; Johann Pütter, deceased, late of Wuppertal, Fed. Rep. of Germany, by Elisabeth Pütter, sole heiress

[73] Assignee: Bayer Aktiengesellschaft, Leverkusen, Fed. Rep. of Germany

[21] Appl. No.: 678,626

[22] Filed: Dec. 6, 1984

[30] Foreign Application Priority Data

Dec. 23, 1983 [DE] Fed. Rep. of Germany ....... 3346571

[51] Int. Cl.⁴ ...................... A61K 9/22; A61K 31/60; A61K 47/00
[52] U.S. Cl. ...................... 424/35; 106/210; 424/19; 424/22; 514/165; 514/778
[58] Field of Search ................................. 424/19–22, 424/35; 514/16, 162, 165, 778; 106/210

[56] References Cited

U.S. PATENT DOCUMENTS

| | | | |
|---|---|---|---|
| 3,034,911 | 5/1982 | McKee et al. | 514/778 |
| 3,101,299 | 8/1963 | Ferrand | 514/165 |
| 3,490,742 | 1/1970 | Nichols et al. | 514/778 |
| 3,622,677 | 11/1971 | Short et al. | 514/778 |
| 3,725,556 | 4/1973 | Hanssen et al. | 514/778 |
| 3,946,110 | 3/1976 | Hill | 514/161 |
| 4,072,535 | 2/1978 | Short et al. | 106/210 |
| 4,086,335 | 4/1978 | Bruscato et al. | 514/165 |
| 4,198,507 | 4/1980 | Barry et al. | 514/869 |
| 4,264,573 | 4/1981 | Powell et al. | 424/22 |
| 4,308,251 | 12/1981 | Dunn et al. | 424/22 |
| 4,328,217 | 5/1982 | Gabby et al. | 424/156 |
| 4,339,428 | 7/1982 | Tencza | 514/165 |
| 4,361,545 | 11/1982 | Powell et al. | 424/22 |
| 4,369,308 | 1/1983 | Trubiano | 106/210 X |
| 4,375,468 | 3/1983 | Dunn | 514/165 |
| 4,401,665 | 8/1983 | Sheinaus et al. | 514/162 |
| 4,439,453 | 3/1984 | Vogel | 424/35 |
| 4,520,009 | 5/1985 | Dunn | 514/161 |
| 4,525,345 | 6/1985 | Dunn et al. | 424/22 |
| 4,539,198 | 9/1985 | Powell et al. | 424/22 |
| 4,551,177 | 11/1985 | Trubiano et al. | 106/210 |

*Primary Examiner*—Shep K. Rose
*Attorney, Agent, or Firm*—Sprung Horn Kramer & Woods

[57] ABSTRACT

A delayed-action acetylsalicylic acid formulation comprising by weight 60 to 90% of acetylsalicylic acid, 8 to 40% pregelatinized starch, and 0 to 30% of additives. The amount of starch controls the rate of release.

3 Claims, No Drawings

DELAYED-ACTION ACETYLSALICYLIC ACID FORMULATIONS FOR ORAL ADMINISTRATION

The present invention relates to solid acetylsalicylic acid formulations for oral administration, with delayed release of the active compound and a sustained action, and also to their preparation.

The magnitude and invariability of the blood level values of a drug which are necessary for a sustained therapeutic action depend on the physiological half-life and on the dissolution and absorption from the drug form. The rate of dissolution can be controlled via the solution parameters of the active compound (particle size, derivatives) or the release from the drug form in the digestive juice.

A delayed release necessary for a sustained action can generally only be achieved by means of expensive galenical measures such as delayed-action coating of crystals, pellets, tablets or capsules, matrix tablets, osmotic systems and the like.

For the indication "treatment of acute attacks of pain", acetylsalicylic acid preparations are required in the pharmacopoeias to have quick disintegration and rapid release. This is generally achieved by processing the active compound, without a binder, with one or more adjuvants promoting the disintegration of the preparation (for example corn starch), to form tablets or capsules.

By contrast, the prophylaxis of thrombosis by inhibition of thrombocyte aggregation requires the acetylsalicylic acid to have a delayed uniform release of the active compound, which, for example in the case of the patent medicine Colfarit ® Tabl. 0.5 g, is achieved by microencapsulation of the ASA crystals. However, this process is very expensive.

The object of the present invention was to find an acetylsalicylic acid preparation, with a delayed-action effect, which is inexpensive to prepare and is additionally distinguished by improved chemical and mechanical stability and also by good gastric tolerance.

Now, the present invention relates to an exceptionally simple process for the preparation of solid delayed-action acetylsalicylic acid formulations which consist only of active compound and simple adjuvants and dissolve completely in a time-dependent manner, and also to the acetylsalicylic acid formulations as such and their use as solid delayed-action formulations.

The present invention thus relates to an acetylsalicylic acid formulation containing 60–90% by weight of acetylsalicylic acid, 8–40% by weight of pregelatinized starch and, if appropriate, 0 to 30% by weight of additives, preferably 70–88% by weight of acetylsalicylic acid and 12–30% by weight of pregelatinized starch.

In particular, the ASA formulation preferably contains 70–80% by weight of acetylsalicylic acid.

The present invention further relates to a process for the preparation of delayed-action formulations which contain acetylsalicylic acid, pregelatinized starch and, if appropriate, additives, wherein the individual constituents are processed to form a tablet mixture, especially granules, mixed and preferably compressed directly to form tablets. In this process, it is preferred to use dry granulation. Processes for conversion to briquettes and for granulation by rolling may be specifically mentioned. Alternatively, this mixture can also be filled into hard gelatine capsules. The hard gelatine can contain colored and/or coloring substances and flavorings, as required.

The present invention further relates to the use of acetylsalicylic acid formulations, consisting of acetylsalicylic acid, pregelatinized starch and, if appropriate, additives, as drugs with delayed absorption, especially as analgesics and anti-inflammatory agents and/or for influencing blood platelet aggregation.

In the sense of the present invention, "pregelatinized starch" is understood as meaning natural starch of any origin which has been converted to a paste by a physical or chemical process and then dried. "Pregelatinized starch" is preferably understood as meaning a starch paste which satisfies the specification of NF XV. NF XV is published as "The National Formulary", fifteenth edition, Official from July 1, 1980, United States Pharmacopical Convention, Inc.

In the sense of the present invention, "additives" are understood as meaning: corn starch (Amylum maylis, Ph. Eur.) or other types of starch (Amyla Ph. Eur., Starch NF XV), cellulose powder (Cellulosi pulvis, DAB 8 Powdered Cellulose, NF XV), microcrystalline cellulose (Microcrystalline Cellulose, NF XV), magnesium stearate (Magnesii Stearas, Ph. Eur. NF XV) or other pharmaceutical adjuvants corresponding to the specifications of the drug handbooks.

The process which has been found makes it possible to adjust the rate of release of acetylsalicylic acid from solid drug forms, within very wide limits, by varying the proportion of pregelatinized starch. For this purpose, the acetylsalicylic acid is intensively mixed with 2–40% by weight, preferably 5–30% by weight and very particularly preferably 10–20% by weight of pregelatinized starch and 0–30% by weight of adjuvants and compressed directly, without any other operations, to form tablets or filled into hard gelatine capsules. This is therefore a very inexpensive process for the preparation of solid delayed-action drug forms for oral administration.

The pregelatinized starch is a fine powder in the dry state and can be handled in this form. On contact with water or predominantly aqueous solutions, it swells very rapidly to give a thixotropic gel.

This process also takes place in the finished drug formulation, the acetylsalicylic acid particles becoming coated by the swelling gel. The acetylsalicylic acid is then released by diffusion of the dissolved molecules through the gel coating, the release thus being dependent on the thickness of the coating, that is to say on the proportion of pregelatinized starch in the formulation. By incorporation of different quantities of pregelatinized starch, it is possible to obtain different rates of release, which, as shown by in vivo experiments, leads to analogous gradations in the blood level curves. The absorption of the acetylsalicylic acid was complete in all the formulations tested, as proved by recovery rates of 94–99% of salicylate in the subjects' urine over 0–32 hours (cf. also Example 1 in this connection).

The few examples which follow are intended to illustrate the present invention in greater detail.

EXAMPLE 1

Tablets having the following compositions are prepared from the corresponding dry mixtures:

|  | A | B | C | D | E |
|---|---|---|---|---|---|
| Acetylsalicylic | 500.0 | 500.0 | 500.0 | 500.0 | 500.0 |

|  | A | B | C | D | E |
|---|---|---|---|---|---|
| acid | | | | | |
| Pregelatinized corn starch | 100.0 | 90.0 | 80.0 | 70.0 | 60.0 |
| Corn starch | — | 10.0 | 20.0 | 30.0 | 40.0 |
| Tablet weight (mg) | 600.0 | 600.0 | 600.0 | 600.0 | 600.0 |

Measurement of the rate of release by the method of the U.S. Pharmacopoeia (Paddle, 900 ml, 0.1 N HCL) gave the following percentages:

| Minutes | A | B | C | D | E |
|---|---|---|---|---|---|
| 15 | 1.4% | 2.9% | 7.0% | 13.3% | 19.7% |
| 30 | 3.5% | 5.1% | 11.1% | 22.0% | 28.4% |
| 60 | 9.9% | 18.5% | 25.0% | 38.0% | 42.5% |
| 90 | 24.4% | 33.9% | 33.0% | 49.5% | 55.5% |
| 120 | 36.8% | 47.2% | 52.7% | 72.0% | 77.4% |

After in each case two fasted subjects had taken a tablet of formulations A, C and E, the change in plasma concentrations as a function of time, determined as total salicylate, and the absorption quota were determined by measuring the quantity of salicylic acid excreted with the urine within 32 hours:

| Minutes | A | C | E | [mg/liter] |
|---|---|---|---|---|
| 15 | 0.46 | 2.62 | 3.10 | |
| 30 | 1.67 | 5.31 | 11.25 | |
| 60 | 2.88 | 7.10 | 26.71 | |
| 120 | 8.59 | 10.73 | 53.79 | |
| 180 | 11.39 | 14.39 | 49.43 | |
| 0-32 hours | 476.8 mg | 472.1 mg | 494.2 mg | |
| | 96.7% | 94.4% | 98.9% | |

The strong dependence of the rate of release on the proportion of pregelatinized starch in the tablets, and the direct correlation with the resulting blood levels, could thus be verified unambiguously.

EXAMPLE 2

Determination of the rates of release from tablets of the compositions:

| | F | G | H |
|---|---|---|---|
| Acetylsalicylic acid | 500.0 | 500.0 | 500.0 |
| Pregelatinized corn starch | 100.0 | 80.0 | 75.0 |
| Cellulose powder | | 10.0 | 15.0 |
| Corn starch | | 10.0 | 10.0 |
| Tablet weight [mg] | 600.0 | 600.0 | 600.0 | gave the following values:

| Minutes | F | G | H |
|---|---|---|---|
| 15 | 5.1% | 14.8% | 28.1% |
| 30 | 12.1% | 20.1% | 36.8% |
| 60 | 24.1% | 35.3% | 62.7% |
| 90 | 39.7% | 53.3% | 82.5% |
| 120 | 51.2% | 70.9% | 89.2% |

A pharmacokinetic study on six male fasted subjects, after each had taken a tablet of formulations G and H, gave the following mean blood levels of acetylsalicylic acid (ASA) and salicylic acid (SAA):

| Time [hours] | Formulation G | | Formulation H | |
|---|---|---|---|---|
| | ASA [mg/liter] | SAA [mg/liter] | ASA [mg/liter] | SAA [mg/liter] |
| 0.25 | 0.548 | 1.530 | 2.522 | 2.962 |
| 0.50 | 1.135 | 5.362 | 4.000 | 15.845 |
| 0.75 | 1.043 | 8.205 | 2.483 | 22.260 |
| 1.00 | 1.002 | 9.618 | 1.958 | 25.428 |
| 1.33 | 1.225 | 12.337 | 1.693 | 28.028 |
| 1.67 | 1.320 | 14.220 | 2.880 | 38.710 |
| 2.00 | 1.612 | 17.802 | 3.636 | 47.688 |
| 3.00 | 1.443 | 27.782 | 1.868 | 57.767 |
| 4.00 | 0.988 | 32.997 | 1.392 | 54.385 |
| 6.00 | 0.095 | 30.137 | 0.157 | 39.462 |
| 8.00 | — | 19.043 | — | 21.810 |
| 24.00 | — | 0.332 | — | 0.383 |

The absorption (recovery rate of salicylate in the urine over 0-32 hours) was 95-97% complete for both formulations and all subjects.

EXAMPLE 3

A mixture consisting of 50 parts of acetylsalicylic acid, 7 parts of pregelatinized corn starch, 2 parts of cellulose powder and 1 part of corn starch is converted to briquettes on a tablet press. The briquettes are comminuted again, mixed and compressed to form the final tablets.

EXAMPLE 4

A mixture consisting of 50 parts of acetylsalicylic acid, 8 parts of pregelatinized corn starch, 1 part of cellulose powder and 1 part of corn starch is granulated dry on a roller press under a roller pressure of between 20 and 50 bar. The granules are comminuted, mixed and compressed to form tablets.

It will be understood that the specification and examples are illustrative but not limitative of the present invention and that other embodiments within the spirit and scope of the invention will suggest themselves to those skilled in the art.

What is claimed:

1. A acetylsalicylic acid directly compressed dry mixture tablet formulation consisting essentially of by weight 60 to 90% of acetylsalicylic acid, 8 to 40% pregelatinized starch, and 0 to 30% of cellulose powder and cornstarch additives.

2. An acetylsalicylic acid formulation according to claim 1, consisting essentially of by weight 70 to 88% of acetylsalicylic acid and 12 to 30% of pregelatinized starch.

3. An acetylsalicylic acid formulation according to claim 1, consisting essentially of about 70 to 80% of acetylsalicylic acid by weight.

* * * * *